United States Patent [19]

Ryono et al.

[11] 4,321,392
[45] Mar. 23, 1982

[54] MERCAPTOACYL DERIVATIVES OF 4-OXAZOLIDINE-CARBOXYLIC ACIDS

[75] Inventors: Denis E. Ryono; Miguel A. Ondetti, both of Princeton, N.J.

[73] Assignee: E. R. Squibb & Sons, Inc., Princeton, N.J.

[21] Appl. No.: 119,079

[22] Filed: Feb. 6, 1980

[51] Int. Cl.³ .................... A61K 31/42; C07D 263/04
[52] U.S. Cl. .................... 548/215; 546/275; 424/263; 424/272
[58] Field of Search .................... 548/215; 546/275

[56] References Cited

U.S. PATENT DOCUMENTS

| 4,105,776 | 8/1978 | Ondetti et al. | 424/274 |
| 4,116,962 | 9/1978 | Ondetti et al. | 260/293.63 |
| 4,154,935 | 5/1979 | Ondetti et al. | 546/189 |
| 4,192,878 | 3/1980 | Ondetti | 424/270 |

FOREIGN PATENT DOCUMENTS 861454  2/1978  Belgium.

55-9060  1/1980  Japan .................... 548/215

OTHER PUBLICATIONS

Wolfe, et al., "Tetrahedron Letters", No. 41, (1979), pp. 3913-3916.
Pettit, et al., "J. C. S.", Perlsin I, pp. 950-954, (1973).

*Primary Examiner*—Anton H. Sutto
*Attorney, Agent, or Firm*—Lawrence S. Levinson; Stephen B. Davis

[57] ABSTRACT

This invention is directed to compounds of the formula

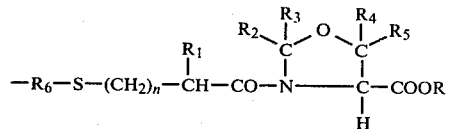

which are useful as hypotensive agents.

7 Claims, No Drawings

MERCAPTOACYL DERIVATIVES OF 4-OXAZOLIDINE-CARBOXYLIC ACIDS

BACKGROUND OF THE INVENTION

Ondetti in Belgian Pat. No. 861,454 disclosed mercaptoacyl derivatives of 4- or 5-thiazolidinecarboxylic acids as well as mercaptoacyl derivatives of 6-member hetero rings such as morpholine and thiamorpholine. These compounds are disclosed as being useful antihypertension agents due to their angiotensin converting enzyme inhibition activity.

Mercaptoacyl derivatives of proline and pipecolic acid are disclosed as useful antihypertension agents due to their angiotensin converting enzyme inhibition activity in U.S. Pat. No. 4,105,776 of Ondetti et al.

Mercaptoacyl derivatives of proline and pipecolic acid wherein the acyl sidechain can be substituted by an alkyl or trifluoromethyl group and the ring can be substituted with one or more halogens are also useful as angiotensin converting enzyme inhibitors as note Ondetti et al, U.S. Pat. No. 4,154,935.

Mercaptoacyl derivatives of proline and pipecolic acid wherein the acyl sidechain can be substituted with a lower alkylthio or mercaptomethyl group are also disclosed as angiotensin converting enzyme inhibitors by Ondetti et al. in U.S. Pat. No. 4,116,962.

SUMMARY OF THE INVENTION

This invention relates to new derivatives of mercaptoacyl 4-oxazolidinecarboxylic acids of formula I and salts thereof

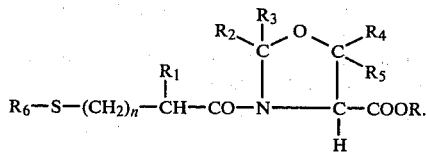

R is hydrogen or lower alkyl.

$R_1$ is hydrogen, lower alkyl, lower alkylthio, mercapto-lower alkylene, or halo substituted lower alkyl.

$R_2$, $R_3$, $R_4$ and $R_5$ are independently selected from hydrogen, lower alkyl, halo substituted lower alkyl,

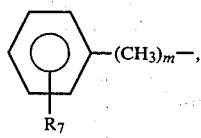

and hereto.

$R_6$ is hydrogen, a hydrolyzably removable protecting group, a chemically removable protecting group, or when $R_1$ is other than mercapto-lower alkylene a sulfide of the formula

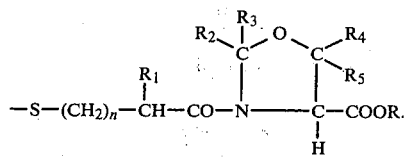

$R_7$ is hydrogen, lower alkyl, lower alkoxy, or halogen.

n is zero or one.

m is zero, one, or two.

The oxazolidine ring contains at least one asymmetric center with other centers possible depending upon the definition of $R_2$, $R_3$, $R_4$ and $R_5$. The mercaptoacyl sidechain can also contain an asymmetric center depending upon the definition of $R_1$. The products can accordingly exist in stereoisomeric forms or as racemic or diastereomeric mixtures thereof. All of these are within the scope of the invention. The synthesis described below can utilize the racemate, a diastereomeric mixture or one of the enantiomers as starting materials. When the racemic or diastereomeric starting material is used in the synthesis procedure, the stereoisomers obtained in the product can be separated by conventional chromatographic or fractional crystallization methods. The asymmetric carbon alpha to the nitrogen and that to which the carboxyl group is attached are preferably in the S configuration.

DETAILED DESCRIPTION OF THE INVENTION

This invention in its broadest aspect relates to the mercaptoacyl derivatives of 4-oxazolidinecarboxylic acid having formula I above and to salts thereof, to compositions containing such compounds and to the method for using such compounds as anti-hypertensive agents.

The term lower alkyl used in the definition of the various symbols are straight or branched chain hydrocarbon radicals having up to four carbon atoms, i.e., methyl, ethyl, propyl, isopropyl, butyl, isobutyl, t-butyl. Methyl and ethyl are the preferred lower alkyl groups. Similarly, the terms lower alkoxy and lower alkylthio refer to such groups attached to an oxygen or sulfur. The term lower alkylene also refers to a group of 1 to 4 carbons such as $-CH_2-$, $-CH_2-CH_2-$, etc.

The term halogen refers to chloro, bromo and fluoro and the term halo substituted lower alkyl refers to such lower alkyl groups described above in which one or more hydrogens have been replaced by chloro, bromo of fluoro groups such as trifluoromethyl, pentafluoroethyl, 2,2,2-trichloroethyl, chloromethyl, bromomethyl, etc.

The term hetero as used in defining the symbols $R_2$ to $R_5$ is used to represent 5 and 6 membered saturated or unsaturated rings having one or more N, O or S atoms which are attached to the remainder of the molecule by way of an available carbon atom. The preferred hetero groups are 2- or 3-thienyl, 2- or 3-furyl, 2-, 3- or 4-pyridine, and 4(or 5)-imidazole.

The term hydrolyzably removable protecting group employed in defining $R_6$ refers to a group that can be removed by conventional hydrolysis or ammonolysis. Acyl groups of the formula

are suitable for this purpose wherein $R_8$ can be lower alkyl of 1 to 4 carbons, halo substituted lower alkyl,

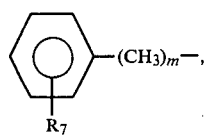

or hetero-$(CH_2)_m$— wherein $R_7$, m, and hereto are as defined above. Preferred groups are the lower alkanoyl groups having up to four carbons, especially acetyl, and benzoyl.

The term chemically removable protecting group employed in defining $R_6$ refers to groups such as p-methoxybenzyl, p-methoxybenzylcarbonyl, trityl, t-butoxycarbonyl, etc. These groups can be removed after the completion of the acylation reaction by various means such as by treatment with trifluoroacetic acid and anisole, sodium and liquid ammonia, or mercuric trifluoroacetate.

With respect to the mercaptoacyl sidechain preferred as final products are those compounds wherein $R_6$ is hydrogen and $R_1$ is hydrogen, lower alkyl of 1 to 4 carbons, especially methyl, trifluoromethyl, methylthio, or mercaptomethyl. Also preferred as both intermediates and final products are the above sidechains wherein $R_6$ is lower alkanoyl or 1 to 4 carbons, especially acetyl, or benzoyl.

With respect to the 4-oxazolidinecarboxylic acid ring preferred compounds are those wherein R is hydrogen; $R_3$ and $R_5$ are hydrogen and $R_2$ and $R_4$ are independently selected from hydrogen, lower alkyl of 1 to 4 carbons, especially methyl, and phenyl; or $R_2$ and $R_3$ are both hydrogen and $R_4$ and $R_5$ are both hydrogen or methyl or one is hydrogen and the other is lower alkyl of 1 to 4 carbons, especially methyl, or phenyl.

Most preferred as final products are the compounds of formula I wherein R is hydrogen, $R_1$ is hydrogen or methyl; n is one; $R_2$, $R_3$, $R_5$ and $R_6$ are all hydrogen; and $R_4$ is hydrogen or methyl.

The compounds of formula I are obtained by coupling the 4-oxazolidinecarboxylic acid or ester of the formula

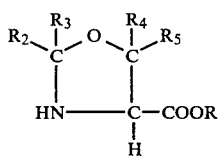

with an acid or its chemical equivalent of the formula

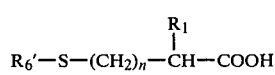

wherein $R_6'$ is hydrogen or a hydrolyzably or chemically removable protecting group to yield the product of the formula

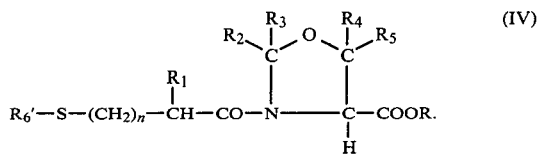

This reaction can be effected in the presence of a coupling agent such as dicyclohexylcarbodiimide or the like, or the acid can be activated by formation of its mixed anhydride, symmetrical anhydride, acid halide, active ester or use of Woodward reagent K, N-ethoxycarbonyl-2-ethoxy-1,2-dihydroquinoline or the like. For a view of the methods of acylation, see Methoden der Organischen Chemie (Houben-Weyl), Vol. XV. part II, page 1 et seq. (1974). Preferably, the acid halide, especially the acid chloride, of formula III is reacted with the acid or methyl ester of formula II.

If the 4-oxazolidinecarboxylic acid of formula II is reacted in the ester form the resulting ester product of formula IV, i.e., R is alkyl, can be converted to the free acid, i.e., R is hydrogen, by conventional means. For example, if R is methyl this ester protecting group can be removed by saponification.

The product of formula IV is preferably isolated and purified by crystallization, e.g., by forming the dicyclohexylamine salt and then converting the salt to the free acid form by passage through a cation exchange column or treatment with an aqueous solution of an acid, such as potassium acid sulfate.

The product of formula IV bearing the acyl group $R_8$—CO— can be converted to the products of formula I wherein $R_6$ is hydrogen by conventional hydrolysis or by ammonolysis.

The compounds of formula I wherein $R_1$ is other than mercapto-lower alkylene and $R_6$ is

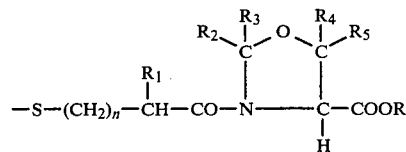

are obtained by directly oxidizing with iodine the compound of formula I wherein $R_6$ is hydrogen.

The esters of formula I, i.e., R is lower alkyl, can be obtained from the carboxylic acid compounds, i.e., R is hydrogen, by conventional esterification procedures, e.g., by esterification with a diazoalkane such as diazomethane, a 1-alkyl-3-p-tolyltriazine such as 1-n-butyl-3-p-tolyltriazene, or the like.

The 4-oxazolidinecarboxylic acids and esters of formula II can be obtained by the condensation of an aldehyde of the formula

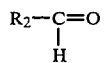

or the ketone of the formula

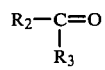

with an α-amino-β-hydroxyamino acid of the formula

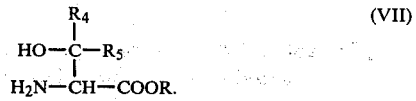 (VII)

See Wolfe et al., Tetrahedron Letters, No. 41, p. 3913-3916 (1979).

Reference is also made to the following publications for additional illustrative methodology for producing starting materials and intermediates: U.S. Pat. Nos. 4,046,889; 4,105,776; 4,154,935; 4,116,962; and JCS Perkin I, p. 950-954 (1973).

The procedures illustrated therein can be utilized as general methods for the synthesis of compounds and separation of isomers which can be utilized in the invention described in this application. Additional illustrative details are found in the examples which serve as models for the preparation of other members of the group.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose, for example aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantanamine, benzathine, or salts derived from amino acids like arginine, lysine or the like. The physiologically acceptable salts like the sodium or potassium salts can be used medicinally as described below and are preferred. These and other salts which are not necessarily physiologically acceptable are useful in isolating or purifying a product acceptable for the purposes described below, as illustrated with the dicyclohexylamine salt in the examples. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compound of formula I wherein $R_6$ is hydrogen,

or the disulfide type substituent, especially wherein $R_6$ is hydrogen, are useful as hypotensive agents. They inhibit the conversion of the decapeptide angiotensin I to angiotensin II and, therefore, are useful in relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds of formula I angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, benzdroflumethiazide, methchlothiazide, trichloromethiazide, polythiazide or benzthiazide, as well as ethacrynic acid, ticrynafen, chlorthalidone, furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative process details are set forth in the following examples for the various reactions. These examples are preferred embodiments and also serve as models for the preparation of other compounds of this invention. The temperatures are given in degrees on the centigrade scale.

EXAMPLE 1

(4S-trans)-3-(3-Mercapto-1-oxopropyl)-5-methyl-4-oxazolidinecarboxylic acid (a) L-trans-5-Methyloxazolidine-4-carboxylic acid, methyl ester A mixture of 5 g. (37 mmol.) of L-threonine, methyl ester and 1.17 g. (38.8 mmol.) of paraformaldehyde in 175 ml. of benzene is refluxed for three hours. The cooled reaction mixture is then filtered over Celite and concentrated in vacuo to yield 5.25 g. of crude L-trans-5-methyloxazolidine-4-carboxylic acid, methyl ester which is employed below without purification.

(b)
(4S-trans)-3-[3-(Acetylthio)-1-oxopropyl]-5-methyl-4-oxazolidinecarboxylic acid, methyl ester The L-trans-5-methyloxazolidine-4-carboxylic acid, methyl ester (5.25 g., 36.2 mmol.) from part (a) is dissolved in 40 ml. of methylene chloride and cooled in an ice-bath under nitrogen. To this cold mixture there is added 5.04 ml. (36.2 mmol.) of triethylamine followed by a solution of 4.83 ml. (36 mmol.) of 3-acetylthiopropanoyl chloride in 16 ml. of methylene chloride which is added over a period of ten minutes. The reaction is kept cold for two hours then at 5° overnight. The precipitated triethylamine hydrochloride salt is filtered off and the reaction mixture is concentrated and applied to 450 g. of Baker silica gel packed in 50:1 (chloroform:methanol). Elution with the same solvent system yields 9.43 g. of an oily slightly impure product. Kugelrohr (bulb to bulb) distillation (120°, <0.001 mm.) of this product is repeated twice to yield pure (4S-trans)-3-[3-(acetylthio)-1-oxopropyl]-5-methyl-4-oxazolidinecarboxylic acid, methyl ester.

(c)
(4S-trans)-3-(3-Mercapto-1-oxopropyl)-5-methyl-4-oxazolidinecarboxylic acid (4S-trans)-3-[3-(Acetylthio)-1-oxopropyl]-5-methyl-4-oxazolidinecarboxylic acid, methyl ester (4.93 g., 17.8 mmol.) is dissolved in 25 ml. of methanol and the resulting solution is cooled in an ice-bath under argon. The cold mixture is then treated with 53.6 ml. of 1 N aqueous sodium hydroxide which is added over a period of ten minutes. Ten minutes after completion of the addition, the reaction mixture is poured into 150 ml. of cold water, acidified to pH 2 with solid potassium bisulfate and saturated with sodium chloride. The aqueous solution is then extracted with two 150 ml. and two 100 ml. portions of ethyl acetate. The combined organic extracts are rinsed with two 50 ml. portions of brine, dried ($Na_2SO_4$), and concentrated in vacuo to afford 4.4 g. of an oil. This oil is treated with 550 ml. of ether and about 15 ml. of methanol to give a clear solution to which is added 4.4 ml. (22.1 mmol.) of dicyclohexylamine to yield 5.3 g. of (4S-trans)-3-(3-mercapto-1-oxopropyl)-5-methyl-4-oxazolidinecarboxylic acid, dicyclohexylamine salt; m.p. 203°–204° (dec.); $[\alpha]_D^{25}$ −55.2° (c=0.5, water).

The dicyclohexylamine salt (5.3 g., 13.2 mmol.) is dissolved in 100 ml. of argon purged water and passed through a 30 equivalent AG50W-X2(H+) cation exchange column. The sulfhydryl active fractions are pooled and immediately partitioned into vials and lyophillized overnight to yield 2.35 g. of (4S-trans)-3-(3-mercapto-1-oxopropyl)-5-methyl-4-oxazolidinecarboxylic acid as an oil.

Analysis Calc'd. for $C_8H_{13}NO_4S$: C, 43.82; H, 5.97; N, 6.39; S, 14.62. Found: C, 43.98; H, 6.18; N, 6.63; S, 13.70.

EXAMPLE 2

[3(S),4S]-3-(3-Mercapto-2-methyl-1-oxopropyl)-5-methyl-4-oxazolidinecarboxylic acid (a)
[3(S),4S]-3-[3-(Acetylthio)-2-methyl-1-oxopropyl]-5-methyl-4-oxazolidinecarboxylic acid, methyl ester Following the procedure of Example 1 but substituting D-3-acetylthio-2-methylpropanoyl chloride for the 3-acetylthiopropanoyl chloride in part (b), one obtains [3(S),4S]-3-[3-(acetylthio)-2-methyl-1-oxopropyl]-5-methyl-4-oxazolidinecarboxylic acid, methyl ester.

(b)
[3(S),4S]-3-(3-Mercapto-2-methyl-1-oxopropyl)-5-methyl-4-oxazolidinecarboxylic acid Treatment of the above methyl ester according to the procedure of Example 1(c) yields [3(S),4S]-3-(3-mercapto-2-methyl-1-oxopropyl)-5-methyl-4-oxazolidinecarboxylic acid.

EXAMPLE 3

[3(S),4S]-3-(3-Mercapto-2-methyl-1-oxopropyl)-4-oxazolidinecarboxylic acid (a)
[3(S),4S]-3-[3-(Acetylthio)-2-methyl-1-oxopropyl]-4-oxazolidinecarboxylic acid, dicyclohexylamine salt A solution of 2.10 g. (20 mmol.) of L-serine in a mixture of 10 ml. of 2 N aqueous sodium hydroxide (20 mmol.) and 1.69 ml. of 37% formaldehyde (20 mmol.) is stirred at 5° overnight. The reaction mixture is then adjusted to pH 7.5, cooled in an ice-water bath and treated with a solution of 3.09 ml. (20 mmol.) of D-3-acetylthio-2-methylpropanoyl chloride in 8 ml. of acetone. 4 ml. of tetrahydrofuran is added to the cold solution to increase the reaction rate. Simultaneous with the addition of the acid chloride solution, a solution of 4 N aqueous sodium hydroxide is added to maintain the pH at 7. The reaction is stirred cold for about thirty minutes after the consumption of base leveled off. The reaction mixture is then diluted to 60 ml. with water and rinsed with two 10 ml. portions of ether. The aqueous layer is cooled and acidified to pH 1.5 with concentrated hydrochloric acid, saturated with sodium chloride and extracted with ether. The combined ether extracts are rinsed with brine, dried ($Na_2SO_4$), and concentrated in vacuo to give 4.4 g. of an impure oily product. The oil is dissolved in ethyl acetate-ether and treated with 20 mmol. of dicyclohexylamine dissolved in ether. The resulting solid (5.1 g.) is recrystallized from methanol-ether to yield 4.0 g. of [3(S),4S]-3-[3-(acetylthio)-2-methyl-1-oxopropyl]-4-oxazolidinecarboxylic acid, dicyclohexylamine salt; m.p. 214°–215°; $[\alpha]_D^{25}$ −91.7° (c=1, methanol).

(b)
[3(S),4S]-3-(3-Mercapto-2-methyl-1-oxopropyl)-4-oxazolidinecarboxylic acid

A suspension of 2.8 g. (6.33 mmol.) of [3(S),4S]-3-[3-(acetylthio)-2-methyl-1-oxopropyl]-4-oxazolidinecarboxylic acid, dicyclohexylamine salt in 15 ml. of water is rapidly stirred under a blanket of argon and cooled in an ice-water bath. The cold mixture is then treated with 17 ml. of 2 N aqueous sodium hydroxide (34 mmol.) which had been chilled in ice-water. The reaction is stirred cold for another twenty minutes, then directly applied to a 200 ml. [AG50W-X2(H)+] cation exchange column (140 meqv.) and the product eluted with water under an atmosphere of nitrogen. The sulfhydryl positive fractions are pooled and lyophillized to give 1.39 g. of an oil. This oil is treated in ethyl acetate-ether with 1.51 ml. (7.6 mmol.) of dicyclohexylamine to yield 2.03 g. of white solid [3(S),4S]-3-(3-mercapto-2-methyl-1-oxopropyl)-4-oxazolidinecarboxylic acid, dicyclohexylamine salt; m.p., 191°–193°; $[\alpha]_D^{25}$ −75.2° (c=0.5, methanol).

This dicyclohexylamine salt (2.0 g., 4.99 mmol.) is converted to the acid by passage through 200 ml. (140 meqv.) of a cation exchange resin [AG50W-X2 (H+)] packed and eluted with water under nitrogen. The sulfhydryl positive fractions are pooled, lyophillized, and the resulting oil partitioned into vials and relyophillized to give 0.986 g. of [3(S),4S]-3-(3-mercapto-2-methyl-1-oxopropyl)-4-oxazolidinecarboxylic acid as an oil.

EXAMPLE 4

(4S)-3-(3-Mercapto-1-oxopropyl)-4-oxazolidinecarboxylic acid

(a)

(4S)-3-[3-(Acetylthio)-1-oxopropyl]-4-oxazolidinecarboxylic acid

Following the procedure of Example 3 but substituting 3-acetylthiopropionyl chloride for the D-3-acetylthio-2-methylthiopropionyl chloride, one obtains (4S)-3-[3-(acetylthio)-1-oxopropyl]-4-oxazolidinecarboxylic acid.

(b)

(4S)-3-(3-Mercapto-1-oxopropyl)-4-oxazolidinecarboxylic acid

The product from part (a) is treated with sodium hydroxide according to the procedure of Example 3 (b) to yield (4S)-3-(3-mercapto-1-oxopropyl)-4-oxazolidinecarboxylic acid.

EXAMPLE 5

(4S-trans)-3-(3-Mercapto-2-trifluoromethyl-1-oxopropyl)-5-methyl-4-oxazolidinecarboxylic acid (a) D,L-3-(Acetylthio)-2-trifluoromethylpropionic acid α-Trifluoromethyl acrylic acid (10 g., 0.071 mole) [prepared according to the procedure set forth in J. Chem. Soc., 1954, p. 371] is cooled in a salt-ice-water bath, stirred and treated portionwise with 5.7 ml. (0.075 mole) of 97% thiolacetic acid. After the addition, the yellow liquid is stirred in the cold for one hour, allowed to warm to room temperature, and distilled to yield 14 g. (91%) of D,L-3-(acetylthio)-2-trifluoromethylpropionic acid as a light yellow oil, b.p. 149°–153°/13 mm. The material solidifies on storing in the cold.

(b) D,L-3-(Acetylthio)-2-trifluoromethylpropionyl chloride

The D,L-3-(acetylthio)-2-trifluoromethylpropionyl acid (7 g., 0.032 mole) is treated with 18 ml. (0.25) of redistilled thionyl chloride and the mixture is refluxed for three hours. After removing the excess thionyl chloride on a rotary evaporator, the residue is distilled to give 6.8 g. of D,L-3-(acetylthio)-2-trifluoromethylpropionyl chloride as a pale yellow oil; b.p. 80°–82°/16 mm.

(c)

(4S-trans)-3-[3-(Acetylthio)-2-trifluoromethyl-1-oxopropyl]-5-methyl-4-oxazolidinecarboxylic acid, methyl ester The acid chloride from part (b) is reacted with 5-methyl-4-oxazolidinecarboxylic acid, methyl ester according to the procedure of Example 1 (b) to yield (4S-trans)-3-[3-(acetylthio)-2-trifluoromethyl-1-oxopropyl]-5-methyl-4-oxazolidinecarboxylic acid, methyl ester.

(d)

(4S-trans)-3-(3-Mercapto-2-trifluoromethyl-1-oxopropyl)-5-methyl-4-oxazolidinecarboxylic acid The product from part (c) is treated with sodium hydroxide according to the procedure of Example 1(c) to yield (4S-trans)-3-(3-mercapto-2-trifluoromethyl-1-oxopropyl)-5-methyl-4-oxazolidinecarboxylic acid. This diastereoisomeric mixture can then be separated into the individual isomers.

EXAMPLES 6–31

Following the procedures of Examples 1 to 5, the 4-oxazolidinecarboxylic acid shown in Col. I is reacted with the acid chloride shown in Col. II to yield the compound shown in Col. III. Treatment with sodium hydroxide yields the product shown in Col. IV.

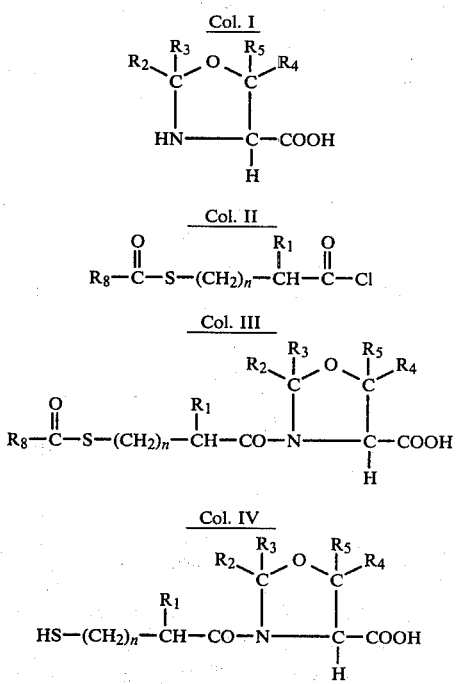

| Example | $R_2$ | $R_3$ | $R_4$ | $R_5$ | $R_1$ | $R_8$ | n |
|---|---|---|---|---|---|---|---|
| 6 | —H | —H | —H | H | —S—CH$_3$ | —CH$_3$ | 1 |
| 7 | —H | —H | —H | —CH$_3$ | —CH$_2$SH | —CH$_3$ | 1 |
| 8 | —CH$_3$ | —H | —H | H | —CH$_3$ | —CH$_3$ | 1 |
| 9 | —H | —H | —CH$_3$ | —CH$_3$ | —H | —C$_6$H$_5$ | 1 |
| 10 | —H | —H | —C$_2$H$_5$ | —H | —H | —(2-thienyl) | 1 |

-continued

| Example | R$_2$ | R$_3$ | R$_4$ | R$_5$ | R$_1$ | R$_8$ | n |
|---|---|---|---|---|---|---|---|
| 11 | —H | —H | —C$_6$H$_5$ | —H | —H | —CH$_3$ | 1 |
| 12 | —C$_6$H$_5$ | —H | —CH$_3$ | —H | —CH$_3$ | —CH$_3$ | 1 |
| 13 | —H | —H | —H | —H | —H | —CH$_3$ | zero |
| 14 | —H | —H | —CH$_2$CCl$_3$ | —H | —CH$_3$ | 2-furyl | 1 |
| 15 | —H | —H | —CF$_3$ | —H | —H | —C$_2$H$_5$ | 1 |
| 16 | —H | —H | —CH$_2$—C$_6$H$_5$ | —H | —CF$_3$ | —CH$_3$ | 1 |
| 17 | —H | —H | —(CH$_2$)$_2$—C$_6$H$_5$ | —H | —H | —C$_2$H$_5$ | 1 |
| 18 | —CH$_3$ | —H | —CH$_3$ | —H | —C$_2$H$_5$ | —C$_6$H$_5$ | 1 |
| 19 | —H | —H | —C$_6$H$_4$—Cl | —H | —H | —CH$_3$ | zero |
| 20 | —H | —H | —CH$_2$—C$_6$H$_4$—CH$_3$ | —H | —CH$_3$ | —CH$_3$ | 1 |
| 21 | —H | —H | —C$_6$H$_4$—OCH$_3$ | —H | —CH$_3$ | —CH$_3$ | 1 |
| 22 | —H | —H | 2-thienyl | —H | —CH$_3$ | —CH$_3$ | 1 |
| 23 | —H | —H | 2-furyl | —H | —CH$_3$ | —CH$_3$ | 1 |
| 24 | —H | —H | 2-thienyl | —H | —H | | 1 |
| 25 | —H | —H | 2-furyl | —CH$_3$ | —H | —CH$_3$ | 1 |
| 26 | —H | —H | 4-piperidinyl | —H | —CH$_3$ | —CH$_3$ | 1 |
| 27 | —H | —H | 2-piperidinyl | —H | —CF$_3$ | —CH$_3$ | 1 |
| 28 | —H | —H | —CH$_3$ | —CH$_3$ | —CH$_3$ | —CH$_3$ | 1 |
| 29 | —H | —H | -n-C$_4$H$_9$ | —H | —H | —C$_6$H$_5$ | 1 |
| 30 | —CH$_3$ | —H | -i-C$_3$H$_7$ | —H | —H | —C$_6$H$_4$—CH$_3$ | zero |
| 31 | H | H | imidazolyl | —H | —CH$_3$ | —CH$_3$ | 1 |

EXAMPLE 32

(S,S)-3,3'-[Dithiobis(1-oxo-3,1-propanediyl)]bis[5-methyl-4-oxazolidinecarboxylic acid]

(4S-trans)-3-(3-Mercapto-1-oxopropyl)-5-methyl-4-oxazolidinecarboxylic acid from Example 1 is dissolved in water and the pH is adjusted to about 6.5 with 1 N sodium hydroxide. To this stirred solution is added dropwise 0.5 M iodine solution in 95% ethanol (6.34 g., iodine/50 ml. solution) while maintaining the pH at 5.5 to 6.5 with 1 N sodium hydroxide. Excess iodine is removed from the reaction mixture with dilute sodium thiosulfate and the solution is then concentrated, cooled and acidified with 1:1 hydrochloric acid. Solvent is added and the mixture is saturated with sodium chloride, stirred, and the layers separated. The organic layer is dried and the solvent evaporated to yield (S,S)-3,3'-[dithiobis(1-oxo-3,1-propanediyl)]bis[5-methyl-4-oxazolidinecarboxylic acid].

EXAMPLE 33

(S,S,S,S)-3,3'-[Dithiobis(2-methyl-1-oxo-3,1-propanediyl)]bis[4-oxazolidinecarboxylic acid]

[3(S),4S]-3-(3-Mercapto-2-methyl-1-oxopropyl)-4-oxazolidinecarboxylic acid from Example 3 is reacted with iodine according to the procedure of Example 32 to yield (S,S,S,S)-3,3'-[dithiobis[2-methyl-1-oxo-3,1-propanediyl]]bis[4-oxazolidinecarboxylic acid].

EXAMPLE 34

(4S-trans)-3-(3-Mercapto-1-oxopropyl)-5-methyl-4-oxazolidinecarboxylic acid, sodium salt A solution of the product of Example 1 is treated with one equivalent of sodium bicarbonate and lyophilized to give (4S-trans)-3-(3-mercapto-1-oxopropyl)-5-methyl-4-oxazolidinecarboxylic acid, sodium salt.

In a similar manner, by employing potassium bicarbonate the corresponding potassium salt is obtained.

EXAMPLE 35

[3(S),4S]-3-(3-Mercapto-2-methyl-1-oxopropyl)-4-oxazolidinecarboxylic acid, sodium salt A solution of the product of Example 3 is treated with one equivalent of sodium bicarbonate and lyophilized to give [3(S),4S]-3-(3-mercapto-2-methyl-1-oxopropyl)-4-oxazolidinecarboxylic acid, sodium salt.

In a similar manner, by employing potassium bicarbonate the corresponding potassium salt is obtained.

EXAMPLE 36

1000 tablets each containing the following ingredients:

| | |
|---|---|
| [3(S),4S]-3-(3-Mercapto-2-methyl-1-oxopropyl)-4-oxazolidinecarboxylic acid, sodium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared (from sufficient bulk quantities) by mixing the [3(S),4S]-3-(3-mercapto-2-methyl-1-oxopropyl)-4-oxazolidinecarboxylic acid, sodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

EXAMPLE 37

Tablets each containing 100 mg. of (4S-trans)-3-(3-mercapto-1-oxopropyl)-5-methyl-4-oxazolidinecarboxylic acid, sodium salt are produced as described in Example 36.

EXAMPLE 38

An injectable solution is produced as follows:

| | |
|---|---|
| [3(S),4S]-3-(3-Mercapto-2-methyl-1-oxopropyl)-4-oxazolidinecarboxylic acid | 500 g. |
| Methyl paraben | 5 g. |
| Propyl paraben | 1 g. |
| Sodium chloride | 25 g. |
| Water for injection qs. | 5 l. |

The active substance, preservatives and sodium chloride are dissolved in 3 liters of water and then the volume is brought up to 5 liters. The solution is filtered through a sterile filter and asceptically filled into presterilized vials which are then closed with presterilized rubber closures. Each vial contains 5 ml. of solution in a concentration of 100 mg. of active ingredient per ml. of solution for injection.

EXAMPLE 39

An injectable solution containing (4S-trans)-3-(3-mercapto-1-oxopropyl)-5-methyl-4-oxazolidiencarboxylic acid is prepared as described in Example 38.

EXAMPLE 40

6000 tablets each containing the following ingredients:

| | |
|---|---|
| [3(S),4S]-3-(3-Mercapto-2-methyl-1-oxopropyl)-4-oxazolidinecarboxylic acid | 100 mg. |
| Avicel (microcrystalline cellulose) | 100 mg. |
| Hydrochlorothiazide | 12.5 mg. |
| Lactose U.S.P. | 113 mg. |
| Corn starch U.S.P. | 17.5 mg. |
| Stearic acid U.S.P. | 7 mg. |
| | 350 mg. | are produced from sufficient bulk quantities by slugging the [3(S),4S]-3-(3-mercapto-2-methyl-1-oxopropyl)-4-oxozolidinecarboxylic acid, Avicel and a portion of the stearic acid. The slugs are ground and passed through a #2 screen, then mixed with the hydrochlorothiazide, lactose, corn starch and remainder of the stearic acid. The mixture is compressed into 350 mg. capsule shaped tablets in a tablet press. The tablets are scored for dividing in half.

EXAMPLE 41

Tablets each containing (4S-trans)-3-(3-mercapto-1-oxopropyl)-5-methyl-4-oxazolidinecarboxylic acid and hydrochlorothiazide can be prepared as described in Example 40.

The product of Examples 2 and 4 to 33 can also be formulated according to the procedures of Examples 36 to 41.

What is claimed is:

1. A compound of the formula

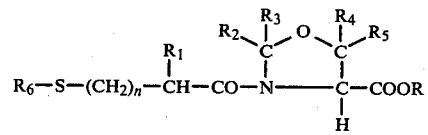

and basic salts thereof wherein:

R is hydrogen or lower alkyl;

$R_1$ is hydrogen, lower alkyl, lower alkylthio, mercapto lower alkylene, or halo substituted lower alkyl;

$R_2$, $R_3$, $R_4$ and $R_5$ are independently selected from the group consisting of hydrogen, lowe alkyl, halo substituted lower alkyl,

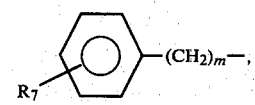

and hetero wherein said hetero is selected from the group consisting of 2-furyl, 3-furyl, 2-thienyl, 3- thienyl, 2-pyridyl, 3-pyridyl, 4-pyridyl, and 4(or 5)-imidazolyl;

$R_7$ is hydrogen, lower alkyl, lower alkoxy, or halogen;

n is zero or one;

m is zero, one or two;

$R_6$ is hydrogen,

p-methoxybenzyl, p-methoxybenzyloxycarbonyl, trityl, t-butoxycarbonyl, or when $R_1$ is other than mercapto-lower alkylene a sulfide of the formula

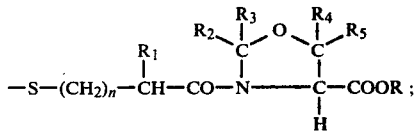

and $R_8$ is lower alkyl, halo substituted lower alkyl,

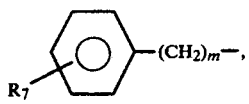

or hetero —$(CH_2)_m$—wherein $R_7$, m, and hetero are as defined above.

2. The compound of claim 1 wherein R is hydrogen; $R_1$ is hydrogen, lower alkyl, trifluoromethyl, methylthio, or mercaptomethyl;

$R_3$ and $R_5$ are both hydrogen and $R_2$ and $R_4$ are independently selected from the group consisting of hydrogen, lower alkyl, and phenyl; or $R_2$ and $R_3$ are both hydrogen and $R_4$ and $R_5$ are both hydrogen or methyl; or $R_2$ and $R_3$ are both hydrogen and one of $R_4$ and $R_5$ is hydrogen and the other is lower alkyl or phenyl; and $R_6$ is hydrogen, lower alkanoyl, or benzoyl.

3. The compound of claim 2 wherein R is hydrogen; $R_1$ is hydrogen or methyl; n is one; $R_2$, $R_3$, $R_5$ and $R_6$ are all hydrogen; and $R_4$ is hydrogen or methyl.

4. The compound of claim 3 wherein $R_1$ is hydrogen and $R_4$ is methyl.

5. The compound of claim 4, (4S-trans)-3-(3-mercapto-1-oxopropyl)-5-methyl-4-oxazolidinecarboxylic acid.

6. The compound of claim 3 wherein $R_1$ is methyl and $R_4$ is hydrogen.

7. The compound of claim 6, [3(S),4S]-3-(3-mercapto-2-methyl-1-oxopropyl)-4-oxazolidinecarboxylic acid.

* * * * *

UNITED STATES PATENT OFFICE
CERTIFICATE OF CORRECTION

PATENT NO. : 4,321,392
DATED : March 23, 1982
INVENTOR(S) : Denis E. Ryono, Miguel A. Ondetti It is certified that error appears in the above-identified patent and that said Letters Patent are hereby corrected as shown below:

Col. 11, Example 26, under $R_4$ the formula should be  --

Col. 11, Example 27, under $R_4$ the formula should be 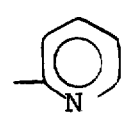 --

Col. 11, Example 31, under $R_4$ the formula should be 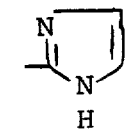 --

Col. 14, line 59, "lowe" should be -- lower --

Signed and Sealed this

Twenty-first Day of December 1982

[SEAL]

Attest:

GERALD J. MOSSINGHOFF

Attesting Officer   Commissioner of Patents and Trademarks